United States Patent [19]

Hershey

[11] 4,386,604
[45] Jun. 7, 1983

[54] DETERMINATION OF THE BASAL METABOLIC RATE OF HUMANS WITH A WHOLE-BODY CALORIMETER

[76] Inventor: Daniel Hershey, 726 Lafayette Ave., Cincinnati, Ohio 45220

[21] Appl. No.: 239,113

[22] Filed: Feb. 27, 1981

[51] Int. Cl.³ .............................................. A61B 5/00
[52] U.S. Cl. ................................... 128/718; 128/736; 374/31
[58] Field of Search ...................... 73/190 CV, 190 R; 128/718, 736; 374/31; 422/51

[56] References Cited

U.S. PATENT DOCUMENTS 2,916,033  12/1959  Coleman .
2,970,041   1/1961  Burlis et al. .
2,984,097   5/1961  Kniazuk et al. .
3,045,665   7/1962  Moyat .
3,396,719   8/1968  Taylor et al. .

OTHER PUBLICATIONS

Hawkins et al., Joun. of Scien. Instr., vol. 35, Dec. 1958, pp. 440–443.
Lawton et al., The Review of Scien. Instr., vol. 25, No. 4, Apr. 1954, pp. 370–377.
Quattvane, The Review of Scientific Instr., vol. 36, No. 6, Jun. 1965, pp. 832–838.
Vadso, Science Tools, vol. 21, No. 23, pp. 18–21, 1974.
Weber et al., Review of Scien. Instr., vol. 47, No. 5, pp. 592–594, May 1976.
Jacobsen et al., Med. & Biol. Eng. & Comp., vol. 20, No. 1, Jan. 1982, pp. 29–36.
Tschegg et al., J. Phys. E. Sci. Instrum., vol. 14, No. 5, 1981, pp. 550–554.
*Medical Physiology*, Edited by Vernon B. Mountcastle, ch. 53, "Energy Exchanger", pp. 1238–1251.
Benzinger, T. H., et al., "Human Calorimetry by Means of the Gradient Principle", J. Applied Physiology, v. 12, Apr. 12, 1958, pp. S1–S24.
Atwater, W. O., and Benedict, F. G., Carnegie Institution of Washington, Publication No. 42, 1905, (Applicant has no copy, but this work is described in the Benzinger article at p. 52 thereof).

*Primary Examiner*—Kyle L. Howell
*Assistant Examiner*—John C. Hanley
*Attorney, Agent, or Firm*—Wood, Herron & Evans

[57] ABSTRACT

The basal metabolic rate (BMR) of a human subject is measured with the subject reclining in a non-adiabatic whole-body calorimeter. Heat losses which occur through the uninsulated wall of the calorimeter chamber during the measurement period are determined in a preliminary calibration step, in the absence of the subject. The BMR measurement is simply made, requiring only the determination of the ambient air and the calorimeter chamber inlet air temperatures, the change of outlet air temperature with time (open circuit), air flow rate, and relative humidity. The use of insulation, sensors in the calorimeter wall and of a circulating water stream to measure temperature increase are unnecessary.

18 Claims, 1 Drawing Figure

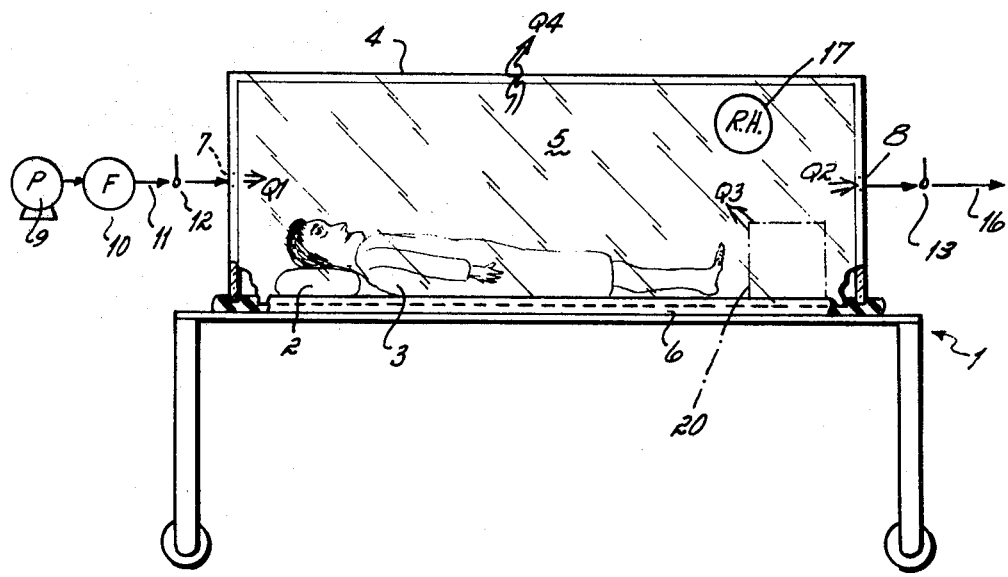

DETERMINATION OF THE BASAL METABOLIC RATE OF HUMANS WITH A WHOLE-BODY CALORIMETER

FIELD OF THE INVENTION

The invention relates to a whole-body calorimetric method and apparatus for measuring the basal metabolic rate (BMR) of a human. The BMR is determined in accordance with this invention from the rates of energy flow into and out of a simple measuring chamber in which the subject can recline and breathe freely. Unlike previous basal metabolism measuring techniques, the invention does not require the use of a mask, gas analysis, an insulated chamber, wall heat loss sensors, air or wall temperature control, or a heat absorbing water stream.

BACKGROUND

The basal metabolic rate is the quantity of heat liberated per unit time by a living organism under prescribed resting conditions. Essentially all of the energy generated by the chemical reactions of the life process within the organism appears as heat energy, because little or no external work is done and having not eaten recently, the amount of energy being stored is zero or negligible. In a resting, fasting state, the basal metabolic activity can be measured as the rate of heat transfer from the body to the environment.

The BMR is usually determined under conditions of as complete mental and physical rest as possible, in a room with comfortable temperature, about 12 to 14 hours after the last meal. Determinations of BMR are useful, for example, in determining the caloric intake required by a given individual to maintain a steady weight. Different persons of the same weight and height can gain or lose weight on the same caloric intake, depending on their metabolic rates and physical activity.

THE PRIOR ART

Heretofore, the energy production of a living organism has most frequently been determined through measurement of the quantity by oxygen consumed in converting foods (within the body) to energy. Since oxygen consumption keeps pace with immediate body needs, including internal chemical reactions, the amount of oxygen consumed per unit time is proportional to the energy liberated. The $O_2$ consumption rate is usually measured with an oxygen filled spirometer and a $CO_2$ absorbing system. That technique requires that a mask be placed tightly over the mouth and nose of the subject being tested in order to capture the gases being exhaled. However, the mask itself, because it is unfamiliar and rather confining, acts as a stimulating factor and by its presence can cause an increase in the metabolic rate of the subject; whereas an accurate determination of the BMR requires that the body be doing no external work and be in a state of rest. Thus that technique can affect the very condition it is intended to measure.

A second problem inherent in the oxygen consumption method for determining BMR is that it depends upon certain assumptions that can introduce errors in a specific case. The amount of energy released per mol of oxygen consumed varies according to the type of heat source (food) being oxidized. Consumption of a given quantity of oxygen will release more or less energy depending upon whether it is acting upon carbohydrates, fat or protein. These are factors which are not easily determinable in a specific subject. The standard determination of BMR by oxygen consumption thus utilizes an average or "standard value" for energy liberation per liter of oxygen consumed per unit time (generally this value is accepted as 4.82 Kcal). More accurate measurement requires data on the specific foods being oxidized, which in turn requires an analysis of the respiratory quotient and the nitrogen excretion. Such determinations are more complex and difficult.

The heat output of a human has also previously been measured directly by calorimetry. One such technique has required a heavily insulated calorimeter in which the heat produced by a human body is measured by change in the temperature of water circulating through the calorimeter. That procedure is complex and expensive. That technique is described in Atwater, W. O. and F. G. Benedict, Carnegie Institution of Washington, publication No. 42, 1905. In another direct calorimetric technique, heat losses through the calorimeter walls are measured by a multiplicity of sensors in the walls, also a complex procedure. That technique is described in Benzinger, T. H., et al, "Human Calorimetry by Means of the Gradient Principle," *Journal of Applied Physiology*, April 1958, pp. S1–S24.

Thus, in general the prior techniques have required the use of face masks, gas separation and analysis, insulated chambers, calorimeter wall sensors, calorimeter temperature stabilizing means, or circulating water heat absorbers.

BRIEF DESCRIPTION OF THE PRESENT INVENTION

This invention is based upon a new method and apparatus for determining basal metabolic rates. It does not require analysis or absorption of any constituents of the respiratory gases, nor does it require use of a mask. Moreover, it does not require an insulated or circulating water calorimeter. In accordance with this new technique and method, the subject reclines in a simple chamber which may be of clear, uninsulated, rigid sheet plastic. Once the calorimeter is calibrated, the only data required to be measured is the ambient temperature around the calorimeter, the inlet airstream temperature, the outlet airstream temperature as a function of time during the test period, relative humidity inside the chamber, and the air flow rate. These can readily and simply be measured. The test can be carried out in one hour or less. Moreover, because the subject can recline within the chamber without a confining mask and under relaxed conditions, he is more likely to be in the state required for accurate basal rate determination.

In any calorimetric measurement, loss of heat through the calorimeter walls must be taken into account. In order to minimize such losses, previous whole body calorimeters have required either an elaborately insulated chamber, or direct measurement of the wall losses, as already noted.

This invention differs in that it does not attempt to prevent such losses, but rather accepts them and makes provision for determining them in a calibration step, whereby they can accurately be taken into account with appropriate calibration constants. The technique depends upon the calibration of heat losses through the calorimeter walls with a known heat source inside, which approximates the heat input of a human body. By such calibration the losses are accurately factored into the BMR determination.

DESCRIPTION OF THE DRAWING

The invention can best be further described and explained by reference to the accompanying drawing, which is a schematic elevation of a preferred form of whole-body calorimeter in accordance with the apparatus of the invention and useful for carrying out the method of the invention.

DETAILED DESCRIPTION

The apparatus includes a base or table 1, which may be on wheels for mobility. The base may be a plastic sheet; a pillow or cushion 2 may be provided on which the subject 3 can recline during the test, but this may act as a heat absorber and thus generally tends to slow the test, which is usually undesirable. A cover 4 is removably positionable over the subject on the platform, to define a test chamber 5 around the subject. The cover may be of clear, rigid plastic (for example, Plexiglas) and need not be insulated to minimize heat loss; insulation is not harmful, but is not needed. The cover forms a hermetic seal with a gasket 6 on the platform. The cover may be hinged to the platform or may be lifted off as by a lift, not shown.

Air is admitted to chamber 5 by an inlet port 7, and exits through an outlet port 8. An air pump 9 supplies air (which may be atmospheric air) at a constant rate, and maintains a very slight positive pressure in the chamber. Pump 9 may be of the type used to bubble air into an aquarium, which for example may deliver about one pound air per hour. The air flow rate entering (or leaving) the chamber is measured by a flowmeter 10, which may be of known type. The temperature of the inlet air is measured adjacent the inlet port 7, suitably just upstream of it in air inlet line 11, by a dry bulb thermometer 12. The temperature of the discharge air is measured by dry bulb thermometer 13, adjacent outlet port 8 in outlet line 16. The air may be discharged directly to atmosphere; unlike prior systems there is no need for a closed or recirculating air system. The relative humidity of the air within the chamber 5 is measured by conventional meter 17.

As already noted, the calorimeter does not retain all body heat within it; nor is it necessary to measure heat losses through the calorimeter walls during the BMR test. Instead, I have discovered a technique whereby heat losses from the calorimeter can be determined through a preliminary calibration step, made without a human subject. The calibration step leads to the determination of certain calibration factors that are effectively constant during the test, and that can be utilized to quantify the heat loss through the calorimeter walls, when a subject is being tested. I have found that given these calibration constants, the BMR of a human subject can then be determined by calculations which are based on easily determined variables of air temperatures, air relative humidity, air flow rate, and the calibration constants.

The required calibration can be carried out with reasonable accuracy, as shown hereinafter, by placing a heating mantle 20 inside the chamber (with no subject present), energizing it to supply heat at a known rate to the chamber, and measuring the rate of heat accumulation in the air flowing through the chamber. The mathematical analysis, upon which the calibration technique and the BMR measurement depend, is set forth below.

In accordance with this invention, both the determination of BMR and the calibration of the calorimeter itself proceed from the heat transport equation, $$\begin{array}{c}\text{rate of} \\ \text{energy} \\ \text{in}\end{array} - \begin{array}{c}\text{rate of} \\ \text{energy} \\ \text{out}\end{array} + \begin{array}{c}\text{rate of} \\ \text{energy} \\ \text{generation}\end{array} - \begin{array}{c}\text{rate of} \\ \text{energy} \\ \text{depletion}\end{array} = \begin{array}{c}\text{rate of} \\ \text{energy} \\ \text{accumulation}\end{array} \quad (1)$$

Using the definitions,
Q1 = enthalpy of the inlet airstream, cal/hr.
Q2 = enthalpy of the outlet airstream, cal/hr
Q3 = heat generated by a heating mantle (used for calibration of the calorimeter), cal/hr
Q4 = heat loss from the whole body calorimeter, cal/hr and substituting, we have, $$Q1 - Q2 + Q3 - Q4 = \frac{\partial U}{\partial t} \quad (2)$$

where U = internal energy of the whole-body calorimeter. Equation 2 can be rewritten as $$\dot{m}1\,Cp1(T1 - T0) - \dot{m}2Cp2(T - T0) + Q3 - (hA + kA/\Delta X)(T - T0) = \quad (3)$$

$$(\rho i\,Vi\,Cvi + \rho w\,Vw\,Cvw + \rho m\,Vm\,Cvm)\frac{\partial T}{\partial t}$$

where
m1 = inlet dry air mass flow rate
m2 = outlet dry air mass flow rate
Cp1 = heat capacity at constant pressure of the inlet airstream
Cp2 = heat capacity at constant pressure of the outlet airstream
T1 = inlet airstream temperature
T0 = ambient temperature surrounding the calorimeter
T = outlet airstream temperature
$\rho i$ = density of the air inside the calorimeter
$\rho w$ = density of the wall material of the calorimeter
$\rho m$ = density of the heating mantle (used in the calibration studies)
Vi = inside volume of the calorimeter
Vw = volume of the wall material of the calorimeter
Vm = volume of the heating mantle inside the calorimeter (where it is used in calibration studies)
Cvi = heat capacity at constant volume of the air inside the calorimeter
Cvw = heat capacity at constant volume of the calorimeter wall material
Cvm = heat capacity at constant volume of the heating mantle inside the calorimeter
k = thermal conductivity of the calorimeter wall material
h = convective heat transfer coefficient for heat loss from the calorimeter to its surroundings
A = calorimeter area for heat loss by conduction and convection
$\Delta X$ = wall thickness of the calorimeter Because the temperature rise of the airstream from inlet to outlet is only a few degrees (Fahrenheit), it can be assumed that $$\dot{m}1\,Cp1 \simeq \dot{m}2\,Cp2 \simeq \dot{m}\,Cp \quad (4)$$

Further, the changes in heat capacity of the air resulting from the changes in composition of the air by respiration of the subject are small.

The calibration constants $\alpha$ and $\beta$ are defined as follows:

$$\alpha = hA + kA/\Delta X \tag{5}$$
= first calibration constant for the calorimeter $$\beta = \rho i\, Vi\, Cvi + \rho w\, Vw\, Cvw + \rho m\, Vm\, Cvm \tag{6}$$
= second calibration constant for the calorimeter Also, $$\gamma = \dot{m}\, Cp = \text{a constant} \tag{7}$$

Substituting equations 5 through 7 into equation 3, we obtain $\gamma(T1 - T) - \alpha(T - T0) + Q_3 = \beta dT/dt$
or, rearranging, $$dT/dt + \left(\frac{\alpha + \gamma}{\beta}\right) T = (\alpha T0 + \gamma T1 + Q_3)/\beta \tag{8}$$

Let $$P = \frac{\alpha + \gamma}{\beta} \tag{9}$$

and $$W = (\alpha T0 + \gamma T1 + Q_3)/\beta \tag{10}$$

Substituting equations 9 and 10 into equation 8, we can get $$dT/dt + Pt = W \tag{11}$$

Equation 11 can be solved with its initial condition where $T=T0$ at $t=0$ \tag{12} to obtain $$T(t) = (T0 - W/P)\exp(-Pt) + W/P \tag{13}$$

For long times, $t \to \infty$, we get from equation 13

$$T\infty = W/P \tag{14}$$

where $T\infty$ represents the temperature of the outlet airstream at steady state and constant $Q_3$.

Substituting equation 14 into 13 and with some rearrangement, we get $$\ln(T\infty - T) = \ln(W/P - T0) - Pt \tag{15}$$

Calibration

For calibration, T0, T1, T∞, T, and Q3 are measured as a function of time, t. From the slope of the plot of ln (T∞ −T) versus t, that is, −P, P can be calculated. Thus with known P and T∞, from equation 14, W can be obtained. Gamma can be calculated from the experimental conditions as shown below by way of example. Let $$\dot{m} = \dot{m}1 = \dot{m}2 \tag{16}$$
$= (35\ l/min)(60\ min/hr)(1/28.32\ ft^3/l)(0.074\ lbm/ft^3)$
$= 5.487\ lbm/hr\ dry\ air$ then $$\gamma = \dot{m}\, Cp = (5.487\ lbm/hr)(0.25\ Btu/lbm\ ^\circ F.) \tag{17}$$
$= 1.37\ Btu/hr\ ^\circ F.$ With known $\gamma$, Q3, P, and W, equations 9 and 10 can be rearranged to give $$\beta = (-\gamma T0 + \gamma T1 + Q_3)/(W - PT0) \tag{18}$$
$$\alpha = P\beta - \gamma \tag{19}$$

and thus we can determine $\beta$, then $\alpha$, that is, the two calibration constants required during the experiments with human subjects. Thus equations 18 and 19 are the working equations for the calibration.

During calibration a heating mantle is placed in the calorimeter. The heating mantle is connected to an adjustable powerstat and wattmeter. With fixed m and $\gamma$, for constant Q3 (adjusted by the powerstat and wattmeter), T0, T1, and T are measured at 5-minute intervals for the first hour. Then additional data are obtained every hour for the next five hours.

From equations 14, 15, 18, and 19 and with the original data, we can get P, W, and the two calibration constants $\alpha$ and $\beta$.

Reference may be had to Hershey and Wang, "A New Age-Scale for Humans," Lexington Books, 1980, for further information and description of this technique. In Appendix C, that book presents a sample calculation of P, W, $\alpha$, and $\beta$ from calibration experiment data. Over a series of 15 runs, $\alpha$ was found to vary by $\pm 4.37\%$, $\beta \pm 11.2\%$, P by $\pm 11.2\%$ and W $\pm 12.8\%$. Since air flow rate is fixed for a given pump, $\gamma$ does not vary.

The Basal Metabolic Rate of a Human Subject

For human subject BMR determination, T0, T1, and T(t) are measured. Using the experimental data and equation 13, the slope of the plot of T(t) versus exp (−Pt), that is, T0−W/P, can be obtained. Since P is known from previous calibration measurements, W can be calculated. The rate of heat given off from the human body in the basal state, Q3, can be calculated from a rearranged form of equation 10, that is $$Q_3 = W\beta - \alpha T0 - \gamma T1 \tag{20}$$

($\alpha$ and $\beta$ may change slightly since the heating mantle and human body have different dimensions and thermal capacities.)

The basal metabolic rate of the human subject can be obtained as follows:

$$BMR = Q_3 + Qv \tag{21}$$

where
Q3 = net rate of body heat released to surroundings
Qv = rate of latent heat absorbed as a result of water evaporation from the skin, lungs and other internal surfaces of the body The Qv quantity can be calculated as shown below.
Let
$\pi$ = barometric pressure
Td1 = inlet dry-bulb air temperature
Td2 = outlet dry-bulb air temperature
Ps1 = vapor pressure of water at Td1
Ps2 = vapor pressure of water at Td2
Hr1 = relative humidity inside the calorimeter at the beginning of the measurement and equal to the inlet air humidity Hr2 = relative humidity inside the calorimeter at the end of the measurement Pw1 = partial pressure of water inside the calorimeter at the beginning of the measurement and equal to the partial pressure of water in the inlet air Pw2 = partial pressure of water inside the calorimeter at the end of the measurement Z1 = pounds of water vapor per pound of dry air inside the calorimeter at the beginning of the measurement and equal to the inlet air value Z2 = pounds of water vapor per pound of dry air inside the calorimeter at the end of the measurement $\Delta Hv$ = average heat of vaporization of water between Td1 and Td2 m = mass flow rate of dry air

We know that $$Pw1 = Ps1 \times Hr1 \quad (22)$$

$$Pw2 = Ps2 \times Hr2 \quad (23)$$

$$Z1 = Pw1/(\pi - Pw1) \quad (24)$$

$$Z2 = Pw2/(\pi - Pw2) \quad (25)$$

and can therefore calculate $Qv$ as $$Qv = m(Z2 - Z1)(\Delta Hv) \quad (26)$$

Thus equations 20–26 are the working equations for human subject experiments.

BMR Experimental Procedure

During the basal metabolic rate measurement, $\alpha$, $\beta$ and $\gamma$ are known. First, the human subject's weight is measured. Then the BMR measurements are made, under uniform conditions, such as:

1. The subject has not been exercising for a period of 30 to 60 minutes prior to the measurement.
2. The subject is in a state of absolute mental and physical rest but awake (the sympathetic nervous system is not overactive).
3. The subject must not have eaten anything during the last 12-hour period prior to the measurement (proteins need up to 12 hours to be completely metabolized).
4. The ambient air temperature must be comfortable, 62° to 87° F. (which prevents stimulation of the sympathetic nervous system).
5. The subject must have a normal body temperature of 98.6° F.
6. The pulse rate and respiration must be below 80 beats per minute and 25 cycles per minute, respectively.
7. The subject should wear a loose-fitting gown to keep the same experimental conditions each time.

During the measurements, the subject reclines comfortably in the whole-body calorimeter. Atmospheric air enters and leaves at a moderate velocity.

Measurements of T0, T1, and T(t) are taken at regular intervals, e.g., about every five minutes, until 45 minutes have elapsed. Dry-bulb temperature and relative humidity are measured at the begining and at the end of the experiment and $Qv$ is thereby calculated. From equations 20 through 26, we can calculate the BMR of human subjects.

The thermometers used to measure T0, T1, and T have an accuracy to 0.1° F. Thus the readings of T0, T1, and T have a relative accuracy of about ±0.2 percent. The $\alpha$ value has about a ±4.4 percent relative accuracy, and the $\beta$ value, about a ±11.2 percent. From equation 20 it is estimated that the Q3 value has about a ±12 percent relative accuracy. The $Qv$ value has about a ±5 percent relative accuracy. Therefore from equation 21 it is estimated that the BMR value has about a ±17 percent accuracy.

Reference is again made to the previously identified book, of which I am a co-author, which in Appendix B gives an example of a typical experiment.

Having described the invention, what is claimed is:

1. A whole-body calorimeter for use in obtaining data for calculating the basal metabolic rate of a human subject, comprising, means presenting a chamber for enclosing the subject to be measured, a base on which the subject can recline in said chamber, an inlet for admitting ambient air into said chamber, an air outlet, said chamber being substantially sealed except for said inlet and outlet, means for establishing a constant, known flow of ambient external air through said chamber from said inlet to said outlet, said flow being discharged to atmosphere, means for measuring the temperature of air external to said chamber, the temperature of air entering said chamber by said inlet, and the temperature of air leaving said chamber by said outlet, means for measuring the relative humidity of air in said chamber, and a heat source comprising an electric heater of known heat output within said chamber for heating air in said chamber at a known energy input rate when no subject is present, in order to calibrate heat losses through the walls of said chamber from said heat source when no subject is present in the chamber, said heat source being inactive when the subject is present in said chamber.

2. The calorimeter of claim 1 further characterized in use by the presence of a temperature gradient through said chamber walls.

3. The calorimeter of claim 1 wherein said means for establishing a flow through said chamber comprises a pump which moves external ambient air through said chamber, said outlet returning the flow to atmosphere.

4. The calorimeter of claim 1 wherein said chamber is defined in part by said base and in part by a cover which is removably seated on said base around said subject.

5. The calorimeter of claim 4 wherein said cover is of rigid, sheet plastic.

6. The calorimeter of claim 4 wherein said cover is transparent.

7. The calorimeter of claim 4 further including means providing an air seal between said base and said cover.

8. The calorimeter of claim 1 wherein said heat source is an electric heater which is removable from said chamber and which is removed when a subject is present in the chamber.

9. The calorimeter of claim 1 wherein the means for measuring temperature of air entering by said inlet and leaving by said outlet comprise dry bulb thermometers in air lines connected to said inlet and to said outlet, respectively.

10. A method of measuring the basal metabolic rate of a human, comprising

A. providing an openable, sealable chamber sized to accommodate a human subject in a resting position therein;

B. calibrating the calorimeter, without a subject in the chamber, by the steps comprising:
 1. establishing a flow of atmospheric air through said chamber from an inlet thereof to an outlet from which said air is discharged to atmosphere;
 2. supplying heat into said chamber at a known rate from a steady heat source in said chamber,
 3. measuring the inlet air temperature, the ambient air temperature, the outlet air temperature as a function of time, the relative humidity in the chamber, and the rate of flow of air through said chamber;
 4. calculating the heat capacity of the air discharged from the outlet; and
 5. from the data obtained in step B3 and the rate at which heat is supplied by said heat source, calculating calibration constants of the chamber, comprising the rate at which heat is lost from the calorimeter surface to its surroundings and the total heat capacity of said calorimeter;

C. de-energizing said heat source;

D. positioning the subject in a resting position within said chamber, and again establishing a flow of air from said inlet through the chamber to the outlet;

E. with said subject in said chamber and air flowing through said chamber, measuring the inlet air temperature, the ambient air temperature, the outlet air temperature as a function of time, the change of relative humidity of air in the chamber with time over the test period, F. calculating the rate at which heat is generated by the subject in the chamber in accordance with the heat transport equation, rate of heat generation by the subject within the calorimeter = rate of energy accumulation within calorimeter − rate of energy supplied to calorimeter by inlet air stream + rate of energy removed from calorimeter through outlet air stream + rate of heat lost through the calorimeter walls, wherein the rates summed in such calculation are calculated from the calibration constants determined in step B5, the heat capacity of air discharged from the outlet with the subject in the chamber, and the measurements obtained in step E, G. calculating the rate of latent heat absorption by evaporation, and H. calculating the basal metabolic rate of the subject by adding the rate at which heat is generated by the subject in chamber, as calculated in step F, and the rate of latent heat absorption by evaporation as calculated in step G.

11. The method of claim 10 wherein heat is transmitted through the walls of said chamber to atmosphere, during steps B and E thereof.

12. The method of claim 10 wherein said air flow through said chamber is established by an air pump.

13. The method of claim 10 wherein the temperature of the chamber interior and exterior walls increases during the measurement by heat transfer from said subject.

14. The method of claim 10 further wherein the three parameters comprising the mass flow rate of dry air through the chamber, the difference between weight of water vapor per unit weight of dry air inside the chamber at the end of the measurement and at the beginning of measurement, and the average heat of vaporization of water between inlet and outlet air temperatures are determined, and the rate of latent heat vaporization by evaporation is calculated as the product of said three parameters.

15. The method of claim 10 wherein the outlet air temperature measurement of step B3 is continued until it becomes constant.

16. The method of claim 10 wherein the rate of energy accumulation within the calorimeter is determined as the product of the rate of change of outlet air temperature times the sum of the heat contents of the air in the chamber, the calorimeter wall and the said heat source.

17. The method of claim 10 wherein the rate of energy supplied to the calorimeter by the inlet air stream is determined as the product of inlet dry air mass flow rate times inlet air stream heat capacity, times the difference between the inlet and the ambient air temperatures.

18. The method of claim 10 wherein the rate of energy removed from the calorimeter through the outlet air stream is determined as the product of outlet dry air mass flow rate times the heat capacity of the outlet air stream times the difference between the outlet and the ambient air temperatures.

* * * * *